United States Patent
Luhta et al.

(10) Patent No.: US 9,314,220 B2
(45) Date of Patent: Apr. 19, 2016

(54) ROTOR AND X-RAY CT SCANNERS

(75) Inventors: Randall Peter Luhta, Cleveland, OH (US); Ronald Sharpless, Cleveland, OH (US); Lester Miller, Hudson, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 985 days.

(21) Appl. No.: 12/808,695

(22) PCT Filed: Dec. 16, 2008

(86) PCT No.: PCT/IB2008/055317
§ 371 (c)(1),
(2), (4) Date: Jun. 17, 2010

(87) PCT Pub. No.: WO2009/081327
PCT Pub. Date: Jul. 2, 2009

(65) Prior Publication Data
US 2010/0303209 A1  Dec. 2, 2010

Related U.S. Application Data

(60) Provisional application No. 61/014,903, filed on Dec. 19, 2007.

(51) Int. Cl.
*A61B 6/00* (2006.01)
*A61B 6/03* (2006.01)

(52) U.S. Cl.
CPC . *A61B 6/56* (2013.01); *A61B 6/035* (2013.01); *A61B 6/4291* (2013.01)

(58) Field of Classification Search
CPC ................................ A61B 6/032; A61B 6/035
USPC .............................................................. 378/19
See application file for complete search history.

(56) References Cited

U.S. PATENT DOCUMENTS

| 4,101,768 | A |   | 7/1978  | Lill              |        |
|-----------|---|---|---------|-------------------|--------|
| 4,132,895 | A | * | 1/1979  | Froggatt          | 378/7  |
| 5,487,098 | A | * | 1/1996  | Dobbs et al.      | 378/19 |
| 6,327,330 | B1|   | 12/2001 | Peter             |        |
| 7,807,981 | B2|   | 10/2010 | Frach et al.      |        |
| 2002/0031201 | A1 | | 3/2002 | Suzuki et al.     |        |
| 2005/0152490 | A1 | | 7/2005 | Shechter          |        |

(Continued)

FOREIGN PATENT DOCUMENTS

JP  2004057507 A  2/2004
WO     9919715 A1  4/1999

(Continued)

*Primary Examiner* — Hoon Song

(57) ABSTRACT

The invention relates to a rotor comprising a radiation source having a focal spot for radiating beam towards a subject, detection means for generating signals responsive to energy attenuation of said beam and a circular body having a cavity for housing the radiation source, and a circle arc-shaped surface on which the detection means are mounted. The circle arc-shaped surface is placed opposite to the cavity with respect to the subject, said cavity comprising an inside surface mounted with a shield for shielding the radiation not towards the subject. In this way, the conventional housing for radiation source and shielding are removed, resulting in reduction of focal spot motion caused by motion of the conventional housing. Furthermore, this invention proposes to mount the detection means directly on the circular body without an intermediate structural housing that reduces the detector modules motion relative to the focal spot.

19 Claims, 3 Drawing Sheets

(56) References Cited

U.S. PATENT DOCUMENTS

2006/0227930 A1* 10/2006 Mattson et al. ............... 378/19
2007/0140417 A1* 6/2007 Yasunaga et al. ............ 378/19

FOREIGN PATENT DOCUMENTS

| WO | 2005096946 A1 | 10/2005 |
| WO | 2006129282 A2 | 12/2006 |

* cited by examiner

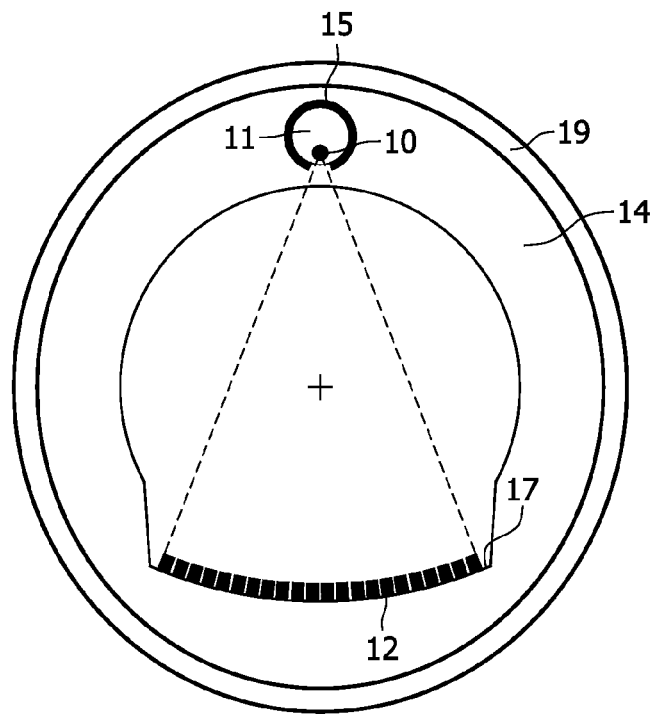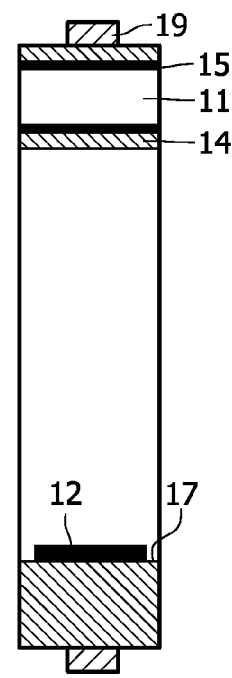
FIG. 1A  FIG. 1B
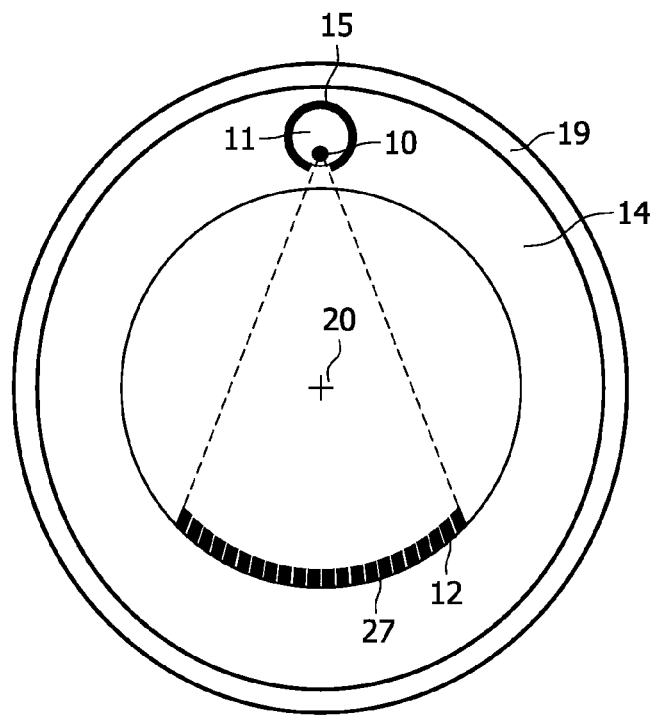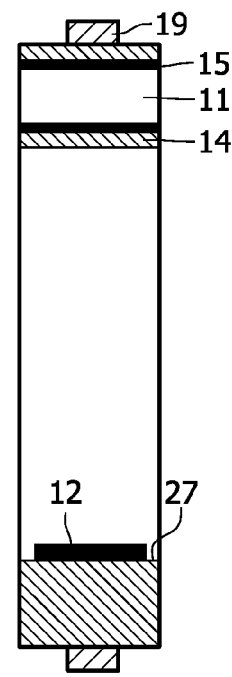
FIG. 2A  FIG. 2B

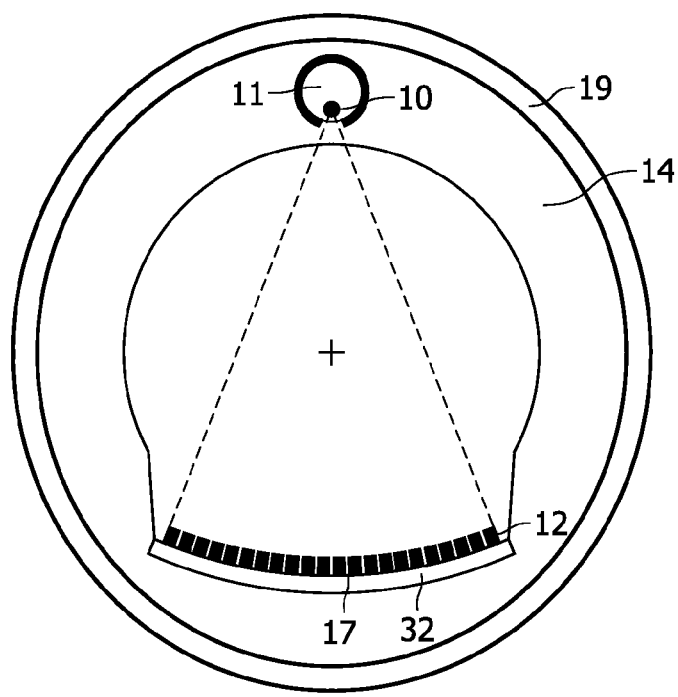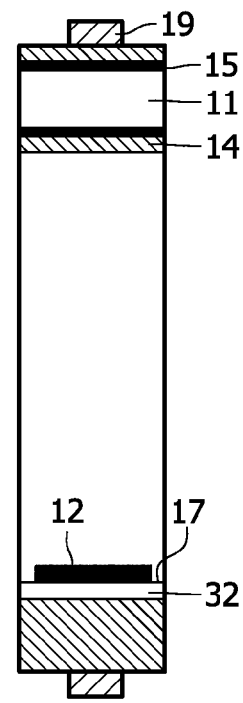
FIG. 3A  FIG. 3B
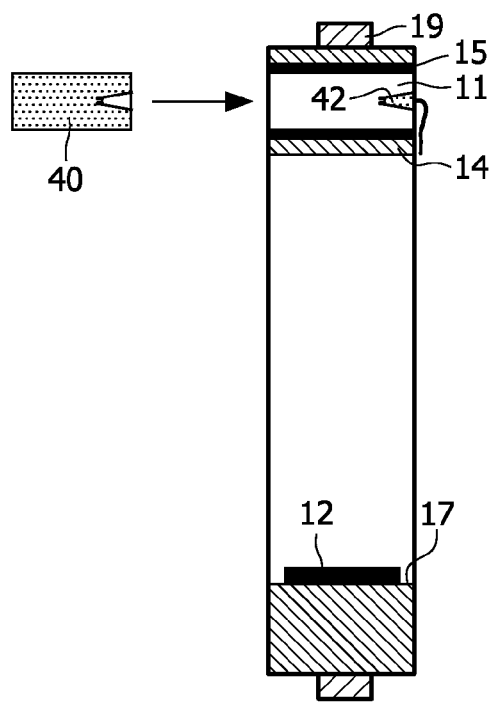
FIG. 4

ROTOR AND X-RAY CT SCANNERS

CROSS REFERENCE TO RELATED APPLICATIONS

This application claims the benefit of U.S. provisional application Ser. No. 61/014,903 filed Dec. 19, 2007, which is incorporated herein by reference.

FIELD OF THE INVENTION

The invention relates to computerized tomography (CT) X-ray imaging and in particular, relates to a rotor and X-ray CT scanners for X-ray CT imaging.

BACKGROUND OF THE INVENTION

In CT X-ray imaging of a patient, X-rays are used to image internal structure and features of a region of the patient body. The imaging is performed by a CT-imaging system, hereinafter referred to as a "CT scanner", which generally comprises an X-ray source and an array of closely spaced X-ray detectors positioned to face the X-ray source. The X-ray source and array of detectors are mounted in a gantry so that a person being imaged with the CT scanners, generally lying on an appropriate support couch, can be positioned within the gantry between the X-ray source and the array of detectors. The gantry and couch are moveable relative to each other so that the X-ray source and detector array can be positioned axially, along a "z-axis", at desired location along the patient's body. The gantry comprises a stationary structure, referred to as a stator, and a rotary element, referred to as a rotor. The rotor is mounted to the stator so that the rotor is rotatable in a plane perpendicular to the z-axis about a center of rotation.

At the present time, X-ray detectors are mounted into a data measurement system cradle, and the cradle is then mounted onto the CT rotor. In the past the rotation speed of the rotor was one revolution per second or less. At these speeds the centrifugal forces on the cradle were moderate and warping of the cradle was not a great issue. However, the rotational speed of the rotor is approaching 4 revolutions per second, which results in 16 times more centrifugal force when compared to one revolution per second. One way to combat the force is to make the cradle structure more substantial, but that may increase cost and cause the cradle to be heavy.

The large force centrifugal has negative effect on CT imaging. As it is well known, in the CT scanner it is very important that the detectors be in precise position relative to the focal spot of the X-rays radiation and the center of the rotation. Furthermore, the anti-scatter grids in the scanner should be aligned such that they all point at the focal spot. The large centrifugal forces on the cradle will cause detectors motion, which may results in image artifacts.

On the other side, at present time the x-ray tube used in CT scanner is a self-contained unit with its own x-ray shielding, structural housing and motor stator. The tube assembly is then mounted on a tube shelf, which may or may not be integral to the rotor itself. When a tube is replaced the x-ray shield and structural housing are also replaced even though these parts did not fail. For some CT scanner, the x-ray tube shelf has been known to move under centrifugal force resulting in an undesirable motion of the focal spot, which introduces image artifacts.

Therefore there is a need to provide a rotor with new structure that reduces relative motion between the focal spot of an X-ray radiation source and detector modules so as to reduce imaging artifacts.

SUMMARY OF THE INVENTION

An object of the invention is to reduce relative motion between the focal spot of a radiation source and detector modules so as to reduce imaging artifacts. This invention achieves the object by providing a rotor, which integrates the radiation source and detector modules into a circular body, the rotor comprising:
  a radiation source having a focal spot (10) for radiating beam towards a subject;
  detection means (12) for generating signals responsive to energy attenuation of said beam;
  a circular body (14) having a cavity (11) for housing the radiation source, and a circle arc-shaped surface (17, 27) on which the detection means (12) are mounted;
wherein the circle arc-shaped surface (17, 27) is placed opposite to the cavity (11) with respect to the subject, said cavity (11) comprising an inside surface mounted with a shield (15) for shielding the radiation not towards the subject.

By mounting the radiation source into the cavity with shielding on the circular body, the conventional housing for radiation source and shield are removed, resulting in reduction of focal spot motion caused by motion of the structure onto which the radiation resource is mounted in conventional CT scanners.

In an embodiment of the invention, the detection means has a plurality of detector modules, which are directly mounted on the circle arc-shaped surface with each of detector modules pointing toward to the focal spot.

By directly mounting the detector modules on the circular body, the centrifugal force on the detection modules is transmitted directly to the circular body instead of through an intermediate structural housing, resulting in reduction of the detector modules motion relative to the focal spot. This also helps mitigate mechanical stack-up error caused by the intermediate structural housing.

In an embodiment, the detection modules are situated on a circle arc-shaped surface. The center of the circle arc-shaped surface is at the rotation center of the rotor, and the detector modules point towards the focal spot of the X-rays radiation. Compared to the conventional arrangement, in which the detection modules are situated on a circle arc centered at the focal spot of the X-rays radiation, this arrangement reduces the thinning of the circular body near the first and last detector module and thus may makes the circular body more substantial.

In an embodiment, the detector modules engage into respective saw-shaped grooves on the circle arc-shaped surface. The arrangement improves alignment of the detector modules with the focal spot.

Modifications and variations thereof, of the rotors, being described, can be carried out by a skilled person on basis of the present description.

DESCRIPTION OF THE DRAWINGS

The above and other objects and features of the present invention will become more apparent from the following detailed description considered in connection with the accompanying drawings, in which:
  FIGS. 1A and 1B are schematic sectional views illustrating an embodiment of a rotor in accordance with the invention.

FIGS. 2A and 2B are schematic sectional views illustrating an exemplary position of the circle arc-shaped surface of the circular body in an embodiment of a rotor in accordance with the invention.

FIGS. 3A and 3B is a schematic sectional view illustrating an exemplary arrangement of the detector modules in an embodiment of a rotor in accordance with the invention.

FIG. 4 is a schematic sectional view illustrating high voltage supply in an embodiment of a rotor in accordance with the invention.

The same reference numerals are used to denote similar parts throughout the figures.

DETAILED DESCRIPTION

Figure 5:
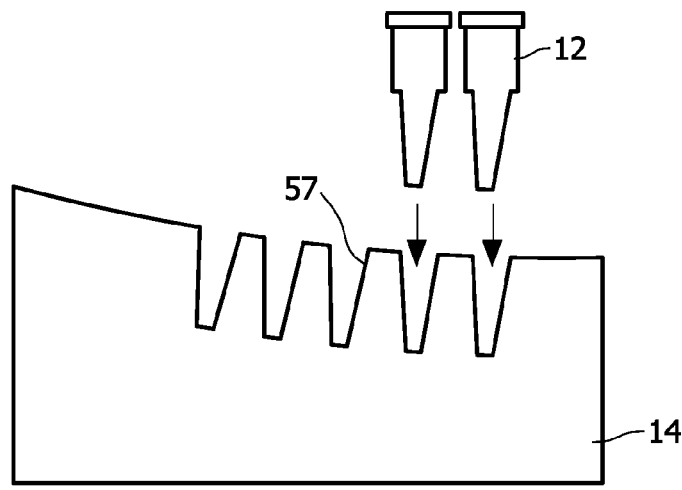
FIG. 5 is a schematic diagram illustrating a first engagement between the detector modules and the circular body in an embodiment of a rotor in accordance with the invention.

FIGS. 1A and 1B are schematic sectional views illustrating an embodiment of a rotor in accordance with the invention. The rotor comprises:
 a radiation source having a focal spot 10 for radiating beam towards a subject;
 detection means 12 for generating signals responsive to energy attenuation of said beam;
 a circular body 14 having a cavity 11 for housing the radiation source, and a circle arc-shaped surface 17, 27 on which the detection means 12 are mounted;
wherein the circle arc-shaped surface 17, 27 is placed opposite to the cavity 11 with respect to the subject, said cavity 11 comprising an inside surface mounted with a shield 15 for shielding the radiation not towards the subject.

Optionally, the rotor comprise bearing 19, which connects the circular body 14 to a stator, which may be fixed in a gantry, and thus enables the rotor to rotate around the subject with support of the stator. The bearing 19 can be on the outside of the rotor or inside of the rotor.

As the cavity 11 in the circular body 14 can house the radiation source without additional structural supporting and the cavity is shaped in such a way that the inside surface is cover certain material that functions as radiation shielding, the new design of the rotor removes conventional structural housing and shielding for radiation source. By mounting the lighter radiation source into the cavity of the circular body, it provides a way to greatly reduce focal spot motion caused by motion of structure, onto which the radiation resource is mounted in conventional CT scanners.

In an embodiment, the detection means 12 has a plurality of detector modules, which are directly mounted on the circle arc-shaped surface 17 with each detector module and associated anti-scatter grid pointing toward to the focal spot. The anti-scatter grid (not shown in the figures) is a self-contained unit of the rotor. It could be assembled to the detection means and then the detection means is attached to the circular body. It could be also first attached to the rotor then the detection means is attached to the circular body over top of the anti-scatter grid. In both cases, the attachments are directly assembled to the circular body without an intermediate structural supporting.

An advantage of directly mounting the detector modules to the circular body is the centrifugal force on the detector would be transmitted directly to the rotor instead of through an intermediate structural supporting like that in conventional products, resulting in reduction on motion of the detector modules relative to the focal spot. Another advantage of directly mounting the detector modules to the circular body is reduction of mechanical stack-up error introduced by the intermediated structural supporting.

Furthermore, an advantage of direct mounting the detector modules to the circular body is in cooling the detectors. The circular body can be used as a large heat sink as the detector modules can be designed to be closely coupled to it. If each detector module incorporates a variable heat source, for instance a resistor, or variable thermal conductance element then the rotor need not be held at a constant temperature. The circular body would of course need to be held below a given temperature.

FIGS. 2A and 2B are schematic sectional views illustrating an exemplary position of the circle arc-shaped surface of the circular body in an embodiment of a rotor in accordance with the invention. Different from the circle arc-shaped surface 17 in FIGS. 1A and 1B, which is centered at the focal spot 10, the center of the circle arc-shaped surface 27 is at the rotation center 20 of the rotor. However, the detector modules and associated anti-scatter grids are still arranged to point toward the focal spot. The arrangement reduces the thinning of the circular body structure near the first and last detector module and thus helps to strengthen it to allow higher rotational speeds to be achieved.

FIGS. 3A and 3B is a schematic sectional view illustrating an exemplary arrangement of the detector modules in an embodiment of a rotor in accordance with the invention. According to FIGS. 3A and 3B, the detection means further comprises digital measurement electronics 32, which is mounted to the circular body. The detector modules 12 are electrically connected to the electronics 32 through connectors or cables.

FIG. 4 is a schematic sectional view illustrating high voltage supply in an embodiment of a rotor in accordance with the invention. The radiation resource comprises an X-ray tube insert 40, e.g. a bare X-ray tube, having a high voltage socket. There is a high voltage plug 42, which is fixed inside the cavity 11. The X-ray tube insert 40 can slides into the cavity 11 in the circular body 14 such that the radiation source can be driven by the high voltage supply.

FIG. 5 is a schematic diagram illustrating a first exemplary engagement between the detector modules and the circular body in an embodiment of a rotor in accordance with the invention. As it is well known, the alignment of the detector module relative to the focal spot relies on the circle arc-shaped surface being accurate. The relative narrow width of the circle arc-shaped surface 17 or 27 means that small errors in the surface will result in large error in angular alignment to the focal spot. The circular body 14 (shown in part) has deep saw-shaped grooves 57 positioned at the circle arc-shaped surface 17 or 27. FIG. 5 shows how the deep grooves 57 in the circular body match long blades on the detector modules 12 to improve the angular alignment of the detector modules to the focal spot. The grooves 57 in the circular body 14 could be roughly cut or cast into place then the final precision shape of the groove set using a single EDM (Electrical Discharge Machining) operation.

Figure 6:
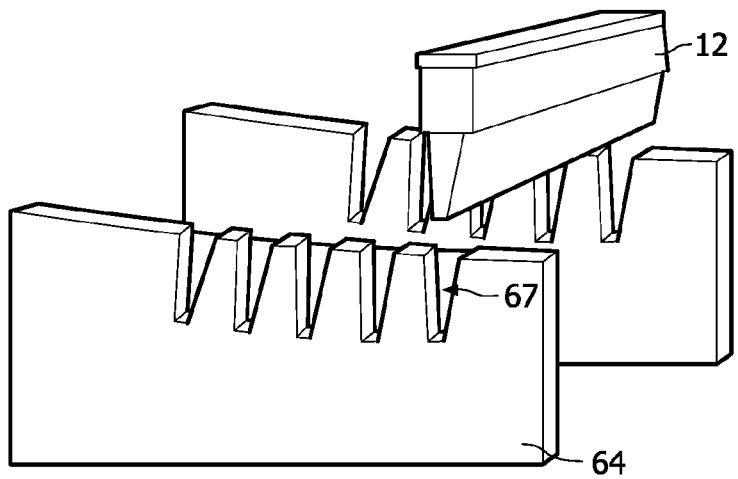
FIG. 6 is a schematic diagram illustrating a second exemplary engagement between the detector modules and the circular body in an embodiment of a rotor in accordance with the invention.

FIG. 6 is a schematic diagram illustrating a second exemplary engagement between the detector modules and the circular body in an embodiment of a rotor in accordance with the invention. The grooves 67 could be formed from photochemically etched metal sheets 64 that are in turn attached to the circular body 14 as a part of the circular body.

Figure 7:
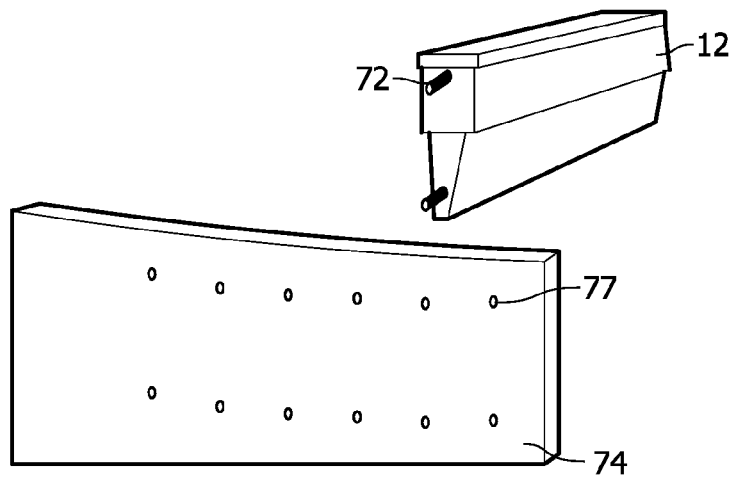
FIG. 7 is a schematic diagram illustrating a third further exemplary engagement between the detector modules and the circular body in an embodiment of a rotor in accordance with the invention.

FIG. 7 is a schematic diagram illustrating a third further exemplary engagement between the detector modules and the circular body in an embodiment of a rotor in accordance with the invention. Either one or two sheets could be used in various configurations at the front and/or the back of the modules 12 in "z-axis".

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements. In the rotor claims enumerating several units, several of these units can be embodied by one and the same item of hardware. The usage of the words first, second and third, etcetera, does not indicate any ordering. These words are to be interpreted as names.

The invention claimed is:

1. A rotor comprising:
   a radiation source having a focal spot for radiating beam towards a subject, wherein the radiation source does not include its own radiation shield;
   detection means for generating signals responsive to energy attenuation of said beam;
   a circular body having a cavity for housing the radiation source, and a circle arc-shaped surface on which the detection means are mounted; wherein the circle arc-shaped surface is placed opposite to the cavity with respect to the subject, said cavity comprising an inside surface mounted with a shield for shielding the radiation not towards the subject.

2. The rotor as claimed in claim 1, wherein the detection means comprise a plurality of detector modules, said detector modules being directly mounted on the circle arc-shape surface with each of the detector module pointing toward to the focal spot.

3. The rotor as claimed in claim 2, wherein the center of the circle arc-shaped surface is at the rotation center of the rotor.

4. The rotor as claimed in claim 2, wherein the center of the circle arc-shaped surface is at the focal spot.

5. The rotor as claimed in claim 2, wherein the circular body comprises saw-shaped grooves on the circle arc-shaped surface, into which the detector modules engage.

6. The rotor as claimed in claim 5, wherein the grooves are shaped using a signal electrical discharge machining operation.

7. The rotor as claimed in claim 2, wherein the circular body has photochemically etched metal sheets attached to the circle arc-shaped surface, said metal sheets having grooves into which the detector modules engage.

8. The rotor as claimed in claim 2, wherein the circular body has photochemically etched metal sheets attached to the circle arc-shaped surface, said metal sheets having holes into which some pins of the detector modules engage.

9. The rotor as claimed in claim 2 further comprising bearings for connecting the circular body to a stator and enabling the circular body to rotate with support of the stator.

10. The rotor as claimed in claim 1, wherein the cavity with the shield and the radiation source are separate structural devices.

11. The rotor as claimed in claim 1, wherein the radiation source is mounted in the cavity.

12. The rotor as claimed in claim 1, wherein the radiation source includes an x-ray tube insert with a high voltage socket and a high voltage plug is fixed inside the cavity, and the high voltage plug plugs into the high voltage socket.

13. The rotor as claimed in claim 12, wherein the cavity is fixedly mounted to the rotor and the radiation source is removably affixed in the cavity.

14. The rotor as claimed in claim 1, wherein the radiation source slides into the cavity, which is previously mounted in the circular body.

15. A method, comprising:
   emitting a radiation via a radiation source located inside a cavity mounted in a circular body of a rotor of an imaging system, wherein the cavity includes an inside surface with a radiation shield and wherein the radiation source does not include its own radiation shield; and
   shielding radiation of the emitted radiation that does not traverse towards a subject or object in an examination region of the imaging system with the radiation shield of the inside of the cavity.

16. The method as claimed in claim 15, wherein the cavity with the shield and the radiation source are separate components.

17. The method as claimed in claim 15, wherein the radiation source slides into the cavity, which is previously mounted in the circular body.

18. The rotor as claimed in claim 1, wherein the radiation source includes an x-ray tube insert with a high voltage socket and a high voltage plug is fixed inside the cavity, and the high voltage plug plugs into the high voltage socket.

19. A rotor comprising:
   a cavity for housing a radiation source, the cavity including:
      an inside surface mounted with a shield for shielding radiation emitted by a focal spot of the radiation and traversing away from an examination region, wherein the radiation source does not include its own radiation shield; and
   a circle arc-shaped surface on which a detector is mounted, wherein the circle arc-shaped surface is placed opposite the cavity across the examination region.

* * * * *